(12) United States Patent
Andersen et al.

(10) Patent No.: US 8,765,994 B2
(45) Date of Patent: Jul. 1, 2014

(54) SHIP 1 MODULATORS

(75) Inventors: Raymond Andersen, Vancouver (CA); David E. Williams, Vancouver (CA); Alice Mui, Burnaby (CA); Christopher Ong, Vancouver (CA); Gerald Krystal, Vancouver (CA); Lu Yang, San Diego, CA (US)

(73) Assignee: The University of British Columbia, Vancouver, BC (CA)

(*) Notice: Subject to any disclaimer, the term of this patent is extended or adjusted under 35 U.S.C. 154(b) by 0 days.

(21) Appl. No.: 13/213,901

(22) Filed: Aug. 19, 2011

(65) Prior Publication Data

US 2012/0129925 A1    May 24, 2012

Related U.S. Application Data

(60) Continuation of application No. 11/871,086, filed on Oct. 11, 2007, now abandoned, which is a division of application No. 10/825,858, filed on Apr. 16, 2004, now abandoned, which is a continuation of application No. PCT/CA03/00571, filed on Apr. 23, 2003, which is a continuation-in-part of application No. PCT/CA02/01550, filed on Oct. 17, 2002.

(60) Provisional application No. 60/329,506, filed on Oct. 17, 2001.

(51) Int. Cl.
*A61K 31/21* (2006.01)
*A61K 31/075* (2006.01)
*C07C 69/76* (2006.01)
*C07C 43/21* (2006.01)
*C07J 63/00* (2006.01)

(52) U.S. Cl.
CPC ...................................... *C07J 63/00* (2013.01)
USPC ................ 560/56; 560/59; 560/60; 568/633; 514/510; 514/719

(58) Field of Classification Search
USPC .................. 514/510, 719; 560/59, 56, 5, 606; 568/633
See application file for complete search history.

(56) References Cited

U.S. PATENT DOCUMENTS

| | | | |
|---|---|---|---|
| 6,238,903 B1 | 5/2001 | Krystal | |
| 2004/0266865 A1* | 12/2004 | Andersen et al. | 514/475 |
| 2008/0090909 A1* | 4/2008 | Andersen et al. | 514/569 |
| 2010/0311094 A1* | 12/2010 | Mui et al. | 435/18 |
| 2010/0323990 A1* | 12/2010 | Andersen et al. | 514/106 |
| 2011/0263539 A1* | 10/2011 | Andersen et al. | 514/143 |
| 2012/0129925 A1* | 5/2012 | Andersen et al. | 514/510 |

FOREIGN PATENT DOCUMENTS

WO    03/033517    4/2003

OTHER PUBLICATIONS

Lawrie, Williams et al. (!979-:23312, HCAPLUS Document No. 90:23312, Original Reference No. 90:3859a,3862a, Title—A novel aromatization reaction of 11-oxolanostanes).*
Johannes C. Liermann et al. (J. Natural Products, 2008, 71, 1654-1656).*
Boreham et al., "Structure and origin of the two major monoaromatic hydrocarbons in a tasmanite oil shale from Tasmania, Australia," *Org. Geochem.* 23(5): 461-466, 1995.
CAS Registry No. 112299-69-1, Jan. 16, 1988 (4 pages).
Corey et al., "Exceptionally Simple Enantioselective Syntheses of Chiral Hexa- and Tetracyclic Polyprenoids of Sedimentary Origin," *Angew. Chem. Int. Ed.* 37(8): 1126-1128, 1998.
Damen et al., "Multiple Forms of the SH2-Containing Inositol Phosphatase, SHIP, Are Generated by C-Terminal Truncation," *Blood* 92(4): 1199-1205, Aug. 15, 1998.
Database CA 'Online! Sorokina et al., "Estrogen and antineoplastic activity in a series of transformed estrone and estradiol analogs," *Izvestiya Akademii Nauk SSSR, Seriya Biologicheskaya* 5: 664-70, 1973, CODENL IANBAM: 002-3329, Database accession No. 80:91450 (Document No. XP002230773).
Freeman et al., "The effect of aromatization on the isotopic compositions of hydrocarbons during early diagenesis," *Org. Geochem.* 21(10/11): 1037-1049, 1994.
Goclik et al., "Pelorol from the Tropical Marine Sponge *Dactylospongia elegans*", *J. Nat. Prod.* 63(8): 1150-1152, 2000.
Harring et al., "Polyene Cascade Cyclizations Mediated by $BF_3 \cdot CH_3NO_2$. An Unusually Efficient Method for the Direct, Stereospecific Synthesis of Polycyclic Intermediates via Cationic Initiation at Non-functionalized 3° Alkenes. An Application to the Total Synthesis of (±)-Taxodione," *Tetrahedron* 50(31): 9229-9254, 1994.
He et al., "Novel cytokine release inhibitors. Part III: truncated analogs of tripterine," *Bioorganic & Medicinal Chemistry Letters* 8(24): 3659-3664, Dec. 15, 1998.
Helgason et al., "Targeted Disruption of *SHIP* leads to hemopoietic perturbations, lung pathology, and a shortened life span," *Genes & Development* 12: 1610-1620, 1998.
Helgason et al., "A Dual Role for Src Homology 2 Domain-containing Inositol-5-Phosphatase (SHIP) in Immunity: Aberrant Development and Enhanced Function of B Lymphocytes in $SHIP^{-/-}$ Mice," *J. Exp. Med.* 191(5): 781-794, Mar. 6, 2000.
Herz et al., "Resin Acids. XV. Oxidative transformations of the levopimaric acid-acetylenedicarboxylic ester adduct," *J. Org. Chem.* 34(5): 1257-1266, 1969.
Huber et al., "The role of SHIP in growth factor induced signalling," *Progress in Biophysics & Molecular Biology* 71: 423-434, 1999.
Ishihara et al., "Enantioselective Biomimetic Cyclization of Homo(polyprenyl)arenes. A New Entry to (+)-Podpcarpa-8, 11, 13-triene Diterpenoids and (−)-Tetracyclic Polyprenoid of Sedimentary Origin," *J. Am. Chem. Soc.* 123(7): 1505-1506, 2001.
Ishihara et al., "Enantio- and Diastereoselective Stepwise Cyclization of Polyprenoids Induced by Chiral and Achiral LBAs. A New Entry to (−)-Ambrox, (+)-Podocarpa-8, 11, 13-triene Diterpenoids, and (−)-Tetracyclic Polyprenoid of Sedimentary Origin," *J. Am. Chem. Soc.* 124(14): 3647-3655, 2002.

(Continued)

*Primary Examiner* — Sabiha N Qazi
(74) *Attorney, Agent, or Firm* — Seed IP Law Group PLLC

(57) ABSTRACT

The present invention includes the use of pelorol, related compounds and pharmaceutical compositions thereof as modulators of SHIP 1 activity. This invention also provides novel terpene compounds capable of modulating SHIP 1 activity and methods of synthesis thereof.

24 Claims, 1 Drawing Sheet

(56) References Cited

OTHER PUBLICATIONS

Kwak et al., "Sesquiterpene Quinols/Quinones from the Micronesian Sponge *Petrosaspongia metachromia*," *J. Nat. Prod.* 63(8): 1153-1156, 2000.

Liu et al., "A specific inhibitor of SH2-containing inositol-5-phosphatase (SHIP)," *Blood* 98: 1225, 2001, LY288975 (Abstract No. 1225).

Mierau et al., "The Dasyscyphins A-C and Niveulone, New Biologically Active Compounds from the Ascomycete Dasyscyphus niveus," *J. Anitbiot.* 59(1):53-56, 2006.

Mitome et al., "Dactyloquinones A and B, new sesquiterpenoid quinones from the Okinawan marine sponge, *Dactylospongia elegans*," *J. Nat. Prod.* 64(12): 1506-8, Dec. 2001.

Mitome et al., "Dactyloquinones C, D and E novel sesquiterpenoid quinones, from the Okinawan marine sponge, *Dactylospongia elegans*," *Tetrahedron* 58(9): 1693-1696, Feb. 25, 2002.

Mukku et al., "New sesquiterpene quinols from a Micronesian sponge, Aka sp," *J. Nat. Prod.* 66(5): 686-689, 2003.

O'Farrell et al., "Stat3-Dependent Induction of $p19^{INK4D}$ by IL-10 Contributes to Inhibition of Macrophage Proliferation," *The Journal of Immunology* 164: 4607-4615, 2000.

Rosales et al., "Regioselective Palladium-Catalyzed Alkylation of Allylic Halides with Benzylic Grignard Reagents. Two-Step Synthesis of Abietane Terpenes and Tetracyclic Polyprenoid Compounds," *J. Org. Chem.* 67(4): 1167-1170, 2002.

Sattler et al., "BCR/ABL Directly Inhibits Expression of SHIP, an SH2-Containing Polyinositol-5-Phosphatase Involved in the Regulation of Hematopoiesis," *Molecular and Cellular Biology* 19(11): 7473-7480, Nov. 1999.

Schaeffer et al., "Neue optisch aktive Kohlenwasserstoffe in Sedimenten: Hinweise auf eine weitgehende biologische Cyclisierung höherer regulärer Polyprenole," *Angew. Chem.* 106(11): 1235-1238, 1994.

* cited by examiner

SHIP 1 MODULATORS

TECHNICAL FIELD OF THE INVENTION

The present invention relates to SHIP 1, a negative regulator of cell proliferation and survival and immune cell activation.

BACKGROUND OF THE INVENTION $SH_2$-containing inositol 5-phosphatase (SHIP 1), selectively hydrolyzes the 5-phosphate from inositol 1,3,4,5-tetraphosphate (IP4) and phosphatalidylinositol 3,4,5-triphosphate (PIPS). U.S. Pat. No. 6,238,903 discloses that SHIP 1 is an enzyme regulator of signaling pathways that control gene expression, cell proliferation, differentiation, activation, and metabolism, particularly of the Ras and phospholipid signaling pathways. SHIP 1 plays an important role in cytokine and immune receptor signal tansduction. SHIP 1 disrupted (SHIP 1−/−) mice exhibit a myeloproliferative phenotype characterized by overproduction of granulocytes and macrophages[1]. SHIP 1−/− mast cells are more prone to IgE and Steel factor induced degranulation, while SHIP 1−/− B cells are resistant to negative regulation by Fc RIIB. SHIP 1 is also involved in the pathogenesis of chronic myelogenous leukemia[2].

Compounds that specifically modulate the activity of SHIP 1 would be useful in the treatment of cell proliferation, hematopoietic and immune disorders, as well as for manipulating SHIP 1 mediated pathways during investigatory and drug discovery testing. To date, no structure of a small molecule SHIP 1 specific modulator has been disclosed.

A sesquiterpene compound termed pelorol may be obtained from various marine sponge species, including *Petrosaspongia metachromia* and *Dactylospongia elegans*. Kwak et al. and Goclik et al. each disclosed the structure of pelorol and its extraction from different marine sponges.[4,5] Pelorol was reported as having weak antitrypanosomal and antiplasmodial effects[5]. The precise structure of pelorol is as follows, with Me representing a methyl group and relative configuration of chiral atoms (C-5,8,9 and 10) shown.

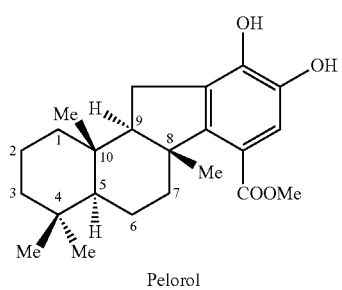

Pelorol

Some reduced and substituted chrysene derivatives similar to pelorol and having the characteristic gem substituted non-aromatic ring of pelorol are known as intermediates or derivatives in the preparation of various polycyclic polyprenols found in shale[6-12], in the preparation of taxodione[13], and in the compound 1,2,3,4,4a,4b,5,6,10b,11,12,12a-dodecahydro-1,1-dimethyl-chrysene[14]. None of these chrysene derivatives are known to have biological activity.

SUMMARY OF THE INVENTION

This invention is based on the discovery that pelorol and related compounds are capable of modulation of SHIP 1 activity.

Some embodiments of this invention provide novel compounds of Formula I and salts thereof. Compounds of Formula I have the structure:

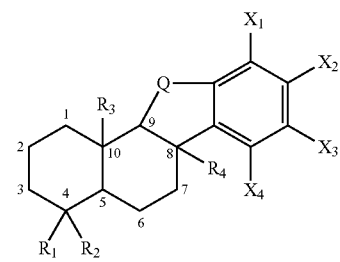

wherein;

$R_1$ and $R_2$ are independently selected from the group consisting of: —$CH_3$, —$CH_2CH_3$, —$CH_2OH$, —$CH_2OR'$, —CHO, —$CO_2H$, and —$CO_2R'$;

$R_3$ and $R_4$ are independently selected from the group consisting of: H, —$CH_3$, —$CH_2CH_3$, —$CH_2OH$, —$CH_2OR'$, —CHO, —$CO_2H$, and —$CO_2R'$;

Q is selected from the group consisting of: —$CH_2$—, —$CY_1Y_2$—, —$CH_2CH_2$—, —CH=CH—, —$CY_1Y_2CY_3Y_4$—, —$CH_2CH_2CH_2$—, —CH=CHCH$_2$—, —CH=CHCY$_1Y_2$—, and —$CY_1Y_2CY_3Y_4CY_5Y_6$—; where $Y_1$, $Y_2$, $Y_3$, $Y_4$, $Y_5$, and $Y_6$ are independently selected from the group consisting of: H, F, Br, Cl, I, OH, OR', and SH; or any one group of $Y_1/Y_2$, $Y_3/Y_4$, and $Y_5/Y_6$ may be =O; or $Y_1/Y_3$ may form an epoxide; and, at least one of $Y_1$, $Y_2$, $Y_3$, $Y_4$, $Y_5$ and $Y_6$ when present, is not H;

$X_1$, $X_2$, $X_3$, and $X_4$ are independently selected from the group consisting of: H, R, OH, —OR, —$CO_2H$, —$CO_2R'$, F, Br, Cl, I, —CN, —$SO_3H$, —$OSO_3H$, $NO_2$, $NH_2$, —NHR, and —$NR_2$; where R is a linear, branched, or cyclic, saturated or unsaturated one to ten carbon alkyl group that is unsubstituted or is substituted with one or more of: OH, =O, SH, F, Br, Cl, I, $NH_2$, —NHR', —$NR'_2$, $NO_2$, —$CO_2H$, —$CO_2R'$, and epoxide;

and R' is a linear, branched, or cyclic, saturated or unsaturated one to ten carbon alkyl group that is unsubstituted or substituted with one or more of: OH, =O, SH, F, Br, Cl, I, $NH_2$, —NHR", —$NR"_2$, $NO_2$ and —$CO_2H$ where R" is a linear, branched, or cyclic, saturated or unsaturated one to ten carbon alkyl group.

Novel compounds of Formula I of this invention do not include the precise structures of previously described gem substituted chrysene derivatives. These previously described compounds include pelorol and compounds having the following structures in which Me is methyl:

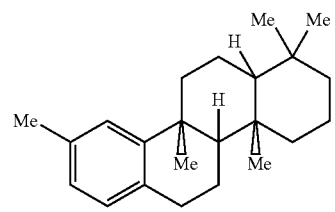

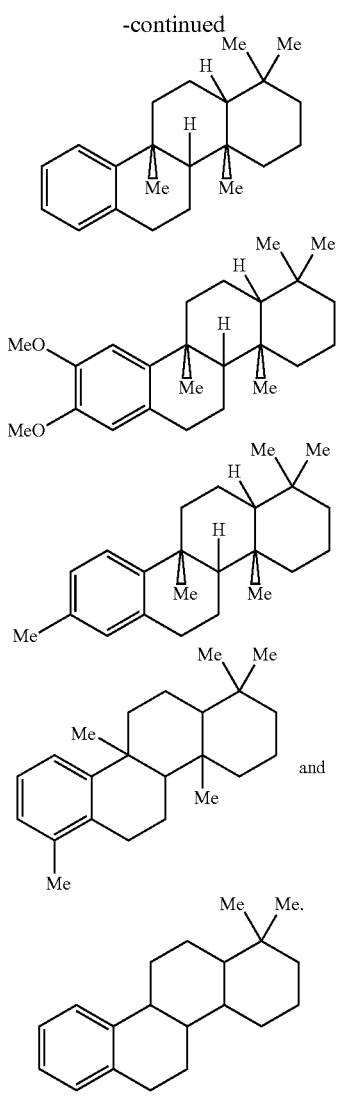

Alternately defined, this invention excludes such previously known specific compounds of Formula I in which each of $R_1$-$R_4$ are methyl; Q is —$CH_2CH_2$—; and, $X_1$-$X_4$ is according to any one of the following definitions:
(a) $X_1$ and $X_2$=OH, $X_3$=H, and $X_4$=—$COOCH_3$;
(b) $X_1$, $X_2$, $X_3$ and $X_4$=H;
(c) $X_1$, $X_2$, and $X_4$=H, and $X_3$=$CH_3$;
(d) $X_1$, $X_3$, and $X_4$=H, and $X_2$=$CH_3$;
(e) $X_2$, $X_3$, and $X_4$=H, and $X_1$=$CH_3$; and
(f) $X_1$ and $X_4$=H, $X_2$ and $X_3$=$OCH_3$.
Also excluded is a compound of Formula I in which $R_1$ and $R_2$=$CH_3$; $R_3$ and $R_4$=H; Q=—$CH_2CH_2$—; and each of $X_1$-$X_4$ is H.

Some embodiments of this invention provide a pharmaceutical composition comprising one or more compounds of Formula I or pharmaceutically acceptable salts thereof, and a pharmaceutically acceptable carrier. Such compositions may comprise previously known compounds of Formula I which have not been known as biologically active compounds suitable for pharmaceutical use.

Some embodiments of this invention provide a method of treatment or prevention of an immune, inflammatory, or neoplastic disorder or condition, comprising administering to a patient in need of such treatment or prevention, an effective amount of a compound of Formula I or pharmaceutically acceptable salt thereof, or a pharmaceutical composition of this invention.

Some embodiments of this invention provide the use of a compound of Formula I or pharmaceutically acceptable salt thereof for modulation of SHIP 1 activity and for preparation of agents for the modulation of SHIP 1 activity. Such modulation may be in vitro or in vivo. Agents for in vivo use include a pharmaceutical composition of this invention as well as agents adapted for in vitro use. The modulation may be for a treatment or prevention of an immune, inflammatory, or neoplastic condition or disorders as described above.

Some compounds of Formula I may be prepared in whole or in part by fractionating biological extracts or by derivatizing available compounds. Alternately, compounds of Formula I may be prepared by total synthesis.

Some embodiments of this invention provide a method of making a compound of Formula IA

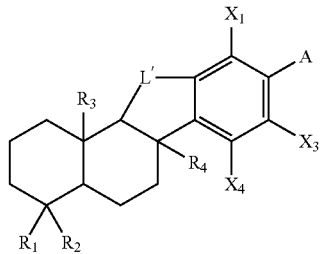

IA in which $R_1$-$R_4$, $X_1$, $X_3$, and $X_4$ are as defined for Formula I, L' is a $C_1$-$C_4$ saturated or unsaturated alkyl linking group; and A is an activating group; comprising reacting a compound of Formula IIA or IIB:

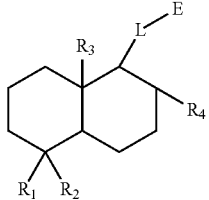

IIA

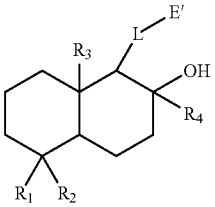

IIB in which L is absent or is a $C_1$-$C_3$ saturated or unsaturated alkyl linking group and E and E' are electrophilic reactive groups; with a compound of Formula III

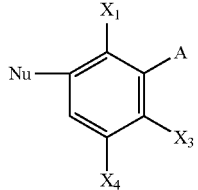

III in which Nu is a group that renders the compound of Formula III nucleophilic at Nu, followed by optional reduction and by hydrolysis, to produce a compound of Formula IV

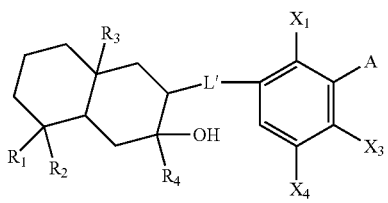

IV and condensing the compound of Formula IV to produce a compound of Formula IA.

L' in compounds of Formula IA may optionally be changed or derivatized to form a desired component Q of Formula I. For example, component L' in compounds of Formula IA produced by the preceding method may have different degrees of saturation or different substituents as compared to Q in a compound of Formula I. In order to reduce the number of atoms in the ring, a compound having an unsaturated L' group could be subjected to oxidizing and reduction steps to reduce the size of the ring in Formula I comprising Q. In addition, functionalities such as ketone, hydroxyl, or other groups may be added to L' to form a desired Q component.

Preferred electrophilic reactive groups for E are lactone, ester, and thioester. A preferred group for E' is carboxyl. More preferably, compounds of Formulas IIA and IIB are as follows.

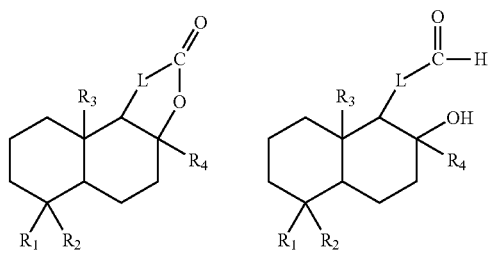

Even more preferably, compounds of Formulas IIA and IIB are as follows:

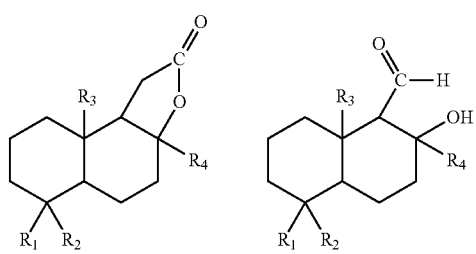

A preferred Nu in compounds of Formula III is lithium which may be substituted onto the ring for a halogen such as bromine. Preferably, A in the compound of Formula III is an activating group such as —OMe or NHAc (Me=methyl and Ac=acetyl) which group may be subsequently converted to a desired substituent for $X_2$ in compounds of Formula I. Substitutents may also be protected, where appropriate with a protecting group such as TBS.

DETAILED DESCRIPTION OF THE INVENTION

Figure 1:
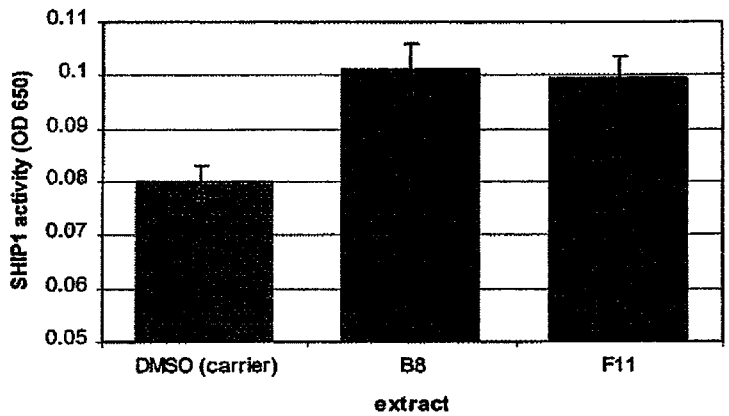
FIG. 1 is a graph depicting the effect of sponge extracts on SHIP 1 enzyme activity in vitro.

In this specification, the following abbreviations will appear: THF (tetrahydrofuran); n-buLi (n-butyly lithium); t-buLi (tert-butyly lithium); $Ph_3PMe$ (methyl triphenyl posphonium bromide); PCC (pyridinium chlorochromate); Ac (acetyl); Me (methyl); Et (ethyl); prop. (propyl); but. (butyl); RT or, r.t. (room temperature); hr. (hour(s)); DMSO (dimethylsulfoxide); DNFB (2,4-dinitrofluorobenzene); LPS (lipopolysaccarhide); TNF-α (Tumor Necrosis Factor Alpha); TBS (tert-butyl dimethylsilyl); and EA (ethyl acetate).

SHIP 1 Modulating Compounds

Compounds of Formula I have chiral centres at C-5, C-8, C-9 and C-10 and may be chiral at C-4 depending upon whether $R_1$ and $R_2$ are different. Compounds of this invention include all stereoisomers and enantiomers of compounds of Formula I. Some embodiments have the same relative configuration of chiral centres as does pelorol or are enantiomers thereof, namely: S, R, R, S; or R, S, S, R (at C-5,8,9 and 10 respectively). Some embodiments have the same absolute configuration as pelorol at chiral centres. Some embodiments have the same relative configuration as pelorol at C-5 and C-10 with independently variable configurations at C-8 and C-9. Some embodiments have the same relative configuration as pelorol at C-5, C-8, and C-10 with variable configuration at C-9. In all cases, the configuration at C-4 (if chiral) may be variable or may be the same relative configuration to the remaining chiral centres as is shown in examples of structures of compounds of Formula I illustrated herein.

In various embodiments of this invention, the compounds may have the limitations in Formula I described above or may have more specific limitations with respect to substituents Q, $R_1$-$R_4$, and $X_1$-$X_4$. Any combination of the following limitations is encompassed by this invention.

(a) Q may be as defined for Formula I except that $Y_{1-6}$ is limited to H or halogen;
(b) Q may be limited to —$CH_2$—, —$CH_2CH_2$—, —CH=CH, —$CH_2$—$CH_2CH_2$— and —CH=$CHCH_2$—;
(c) Q may be limited to H or saturated moieties in the limitation of Formula I, or according to the limitations of paragraph (a) or (b) above;
(d) Q may be limited to a one or two carbon skeleton within the limitations of Formula I, or according to the limitations of any of paragraphs (a)-(c) above;
(e) one or both of $R_1$ and $R_2$ may be limited to methyl, ethyl, —$CH_2OH$ or —$CH_2OR$;
(f) R' in one or both of $R_1$ and $R_2$ according to Formula I, or the limitation of paragraph (e) above, may be limited to methyl, ethyl, propyl or butyl;
(g) one or both of $R_1$ and $R_2$ may be limited to methyl or ethyl;
(h) one or both of $R_1$ and $R_2$ may be limited to methyl;
(i) R and R' in any one or more of $X_1$-$X_4$ may be limited to unsubstituted methyl, ethyl, propyl or butyl;
(j) one or more of $X_1$-$X_3$ may be limited to H, R, OH, OR, halogen, —$CONH_2$, —CONHR', —$COR'_2$, NHR or $NR_2$ where R and R' are limited as in Formula I, or R and R' may be according to paragraph (i) above;

(k) one or more of $X_1$-$X_3$ is limited to H, OH, OR, —$CONH_2$, —CONHR', and —COR'$_2$, where R and R' are as in Formula I, or R and R' may be limited according to paragraph (i) above;

(l) one or more of $X_1$-$X_3$ may be limited to H, OH, and $OCH_3$;

(m) $X_4$ may be limited to H, R, OH, OR, $CO_2H$ or —$CO_2R'$, with R and R' as in Formula I, or R and R' may be limited according to paragraph (i) above;

(n) $X_4$ may be limited to H, R, OH, $OCH_3$, —$CO_2H$ and —$CO_2R'$ with R and R' limited according to paragraph (i) above; and, (o) $X_4$ may be limited to H, R, OH, $OCH_3$, —$CO_2H$ or —$CO_2CH_3$.

The following specific structures are embodiments of this invention. In some cases, variability at $X_1$, $X_2$, and $X_4$ is shown with reference to substituents identified as R, Z, and Y, which for the purposes of the illustrated compounds are defined below. Although relative stereochemistry is illustrated for each structure, the configuration of chiral centres may vary according to any of the embodiments based on chirality described above.

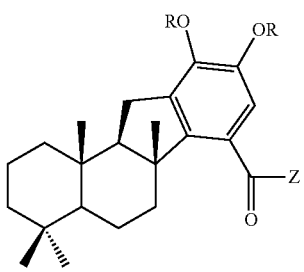

R = H and Me, Et, Prop, But, etc.
Z = OH, OR, $NH_2$, NRH, $NR_2$

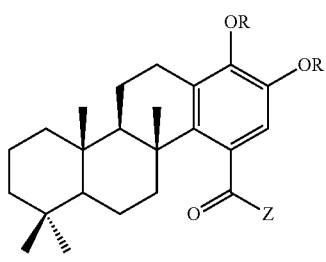

R = H and Me, Et, Prop, But, etc.
Z = OH, OR, $NH_2$, NRH, $NR_2$

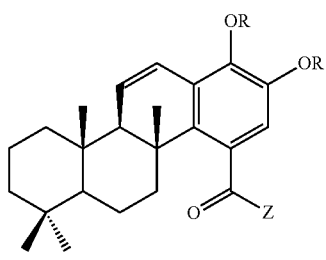

R = H and Me, Et, Prop, But, etc.
Z = OH, OR, $NH_2$, NRH, $NR_2$

-continued

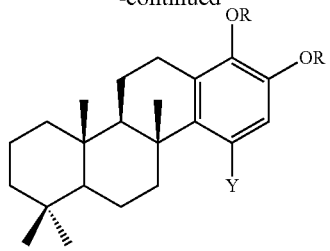

R = H and Me, Et, Prop, But, etc.
Y = H, Me, Et, Prop, But, etc. CHO, $CH_2OR$

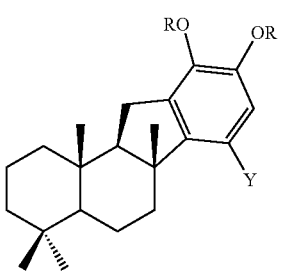

R = H and Me, Et, Prop, But, etc.
Y = H, Me, Et, Prop, But, etc. CHO, $CH_2OR$

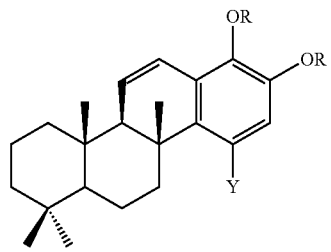

R = H and Me, Et, Prop, But, etc.
Y = H, Me, Et, Prop, But, etc. CHO, $CH_2OR$

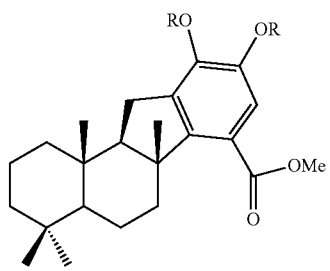

R = H Peterol
R = Me DimethoxyPeterol

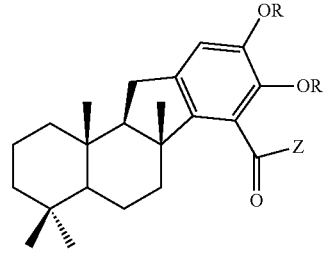

R = H and Me, Et, Prop, But, etc.
Z = OH, OR, $NH_2$, NRH, $NR_2$

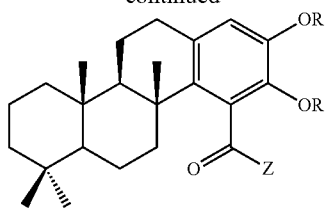
R = H and Me, Et, Prop, But, etc.
Z = OH, OR, NH₂, NRH, NR₂
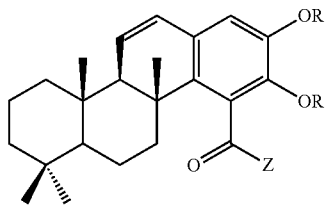
R = H and Me, Et, Prop, But, etc.
Z = OH, OR, NH₂, NRH, NR₂
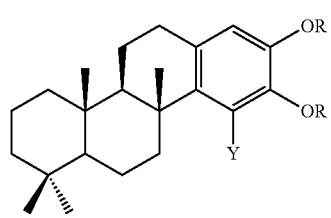
R = H and Me, Et, Prop, But, etc.
Y = H, Me, Et, Prop, But, etc. CHO, CH₂OR
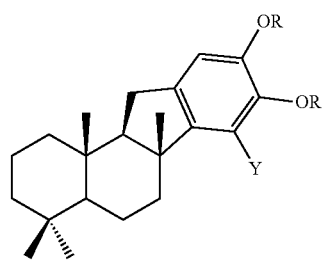
R = H and Me, Et, Prop, But, etc.
Y = H, Me, Et, Prop, But, etc. CHO, CH₂OR
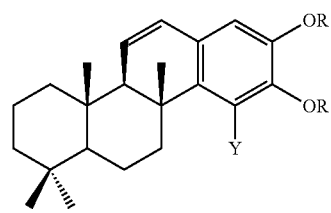
R = H and Me, Et, Prop, But, etc.
Y = H, Me, Et, Prop, But, etc. CHO, CH₂OY
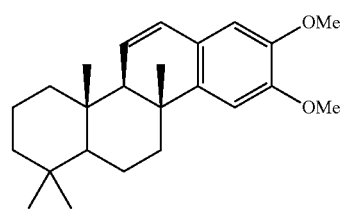
PNSR-4A
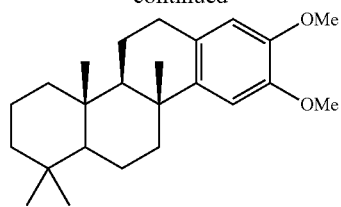
PNSR-5A
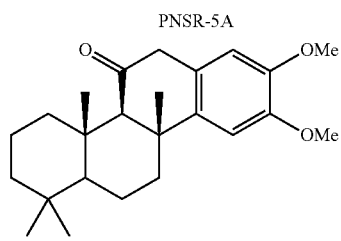
PNSR-6A
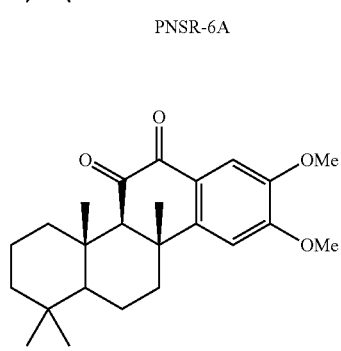
PNSR-8A
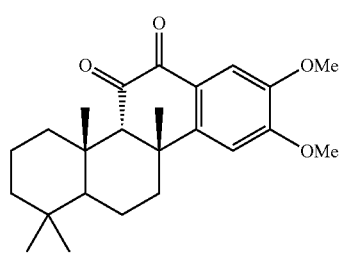
PNSR-9A
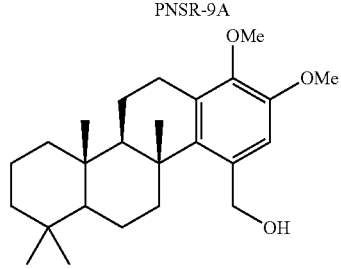
PNSR-11A
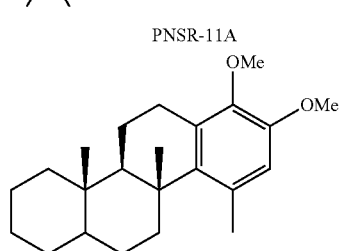
PNSR-14A

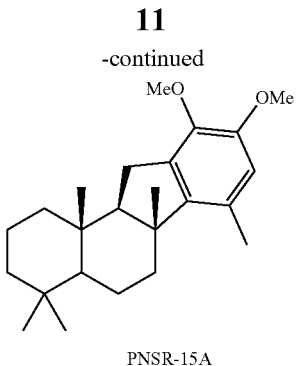

PNSR-15A

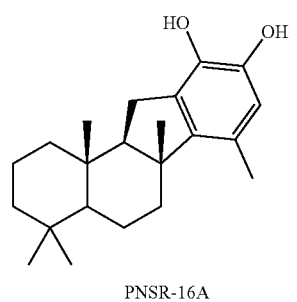

PNSR-16A

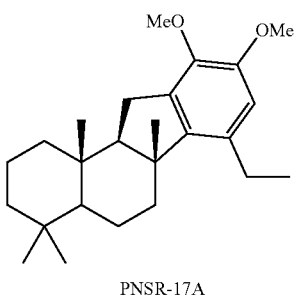

PNSR-17A

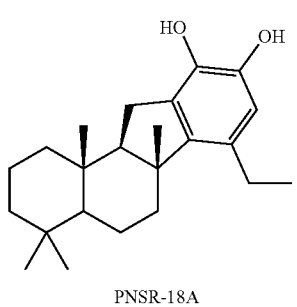

PNSR-18A

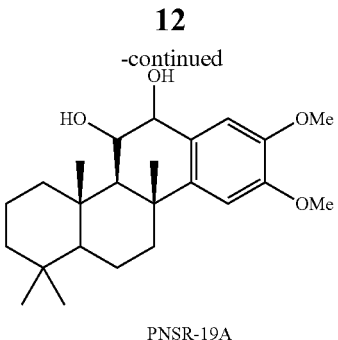

PNSR-19A

Sources of Compounds and Assays for Activity

Pelorol may be obtained from natural sources as taught in the prior art and in the Example 1 herein. Solvent fractionation and/or chromatography may be employed. It is also possible to modify pelorol or other available compounds such as chrysene derivatives by known chemical methodologies to add, remove, or replace substituents in order to produce components of Formula I. Examples of such derivatization steps as applied to different compounds of Formula I are shown in more detail below.

The presence of SHIP 1 modulating compounds in a preparation may be determined by use of a variety of assays, including direct monitoring of a change in activity of SHIP 1 enzyme such as by the methodology disclosed in Example 1 and FIG. 1 or by biological assays which may be readily adapted from known procedures, including cell or animal based assays which monitor changes in: nitric oxide production from activated macrophages; IgE induced mast cell degranulation; LPS induced macrophage activation; TNF-α expression or activity. In addition, standard assays for agents which mediate inflammatory activity in living subjects may be employed.

Adaptation of these assays is facilitated by the availability of SHIP $1^{-/-}$ and SHIP $1^{+/-}$ mice[15,16] and bone marrow derived macrophages[17]. In addition, the availability of anti-SHIP 1 antibodies[18] facilitates use of immunoassay formats. Such assays may also be used to assess activity of compounds prepared by total synthesis, as described herein.

Total Synthesis of Compounds

A synthetic scheme for making pelorol and other compounds of Formula I is provided herein. Tables (1-2) provide detailed examples of two embodiments of such a synthesis with examples of different compounds of Formula I which may be prepared. The compound shown in the Tables that is identical to pelorol except that the ring adjacent the aromatic ring has six members, is termed "homopelorol". Compounds having a six-membered ring are termed "homopelorol analogs". Compounds having a five-membered ring other than pelorol are termed herein, "pelorol analogs".

In the synthesis methods shown in Tables 1 and 2, compounds of Formula IIA shown therein are conveniently based on sclareolide as a starting material. Appropriate derivatives of sclareolide providing desired $R_1$-$R_4$ substituents may be employed. In the aromatic compound of Formula III shown in the Tables, Nu is preferably lithium. $X_2$ in the starting compound of Formula III is preferably an activating group such as —OMe or —NHAc. $X_1$-$X_4$ may remain as found in the starting material or be appropriately altered to provide the desired substituents for the end product. Protecting groups may be employed on $R_1$-$R_4$ or $X_1$, $X_3$, or $X_4$. An example of derivatization of the ring comprising L' in Formula IA to produce a desired component Q of Formula I is illustrated in Table 2 where oxidation (e.g. by treatment with $OsO_4$ followed by treatment with an acid such as HCl) is performed to provide a ketone substituent on the ring.

TABLE 1
Synthesis of Pelorol and Pelorol Analogs
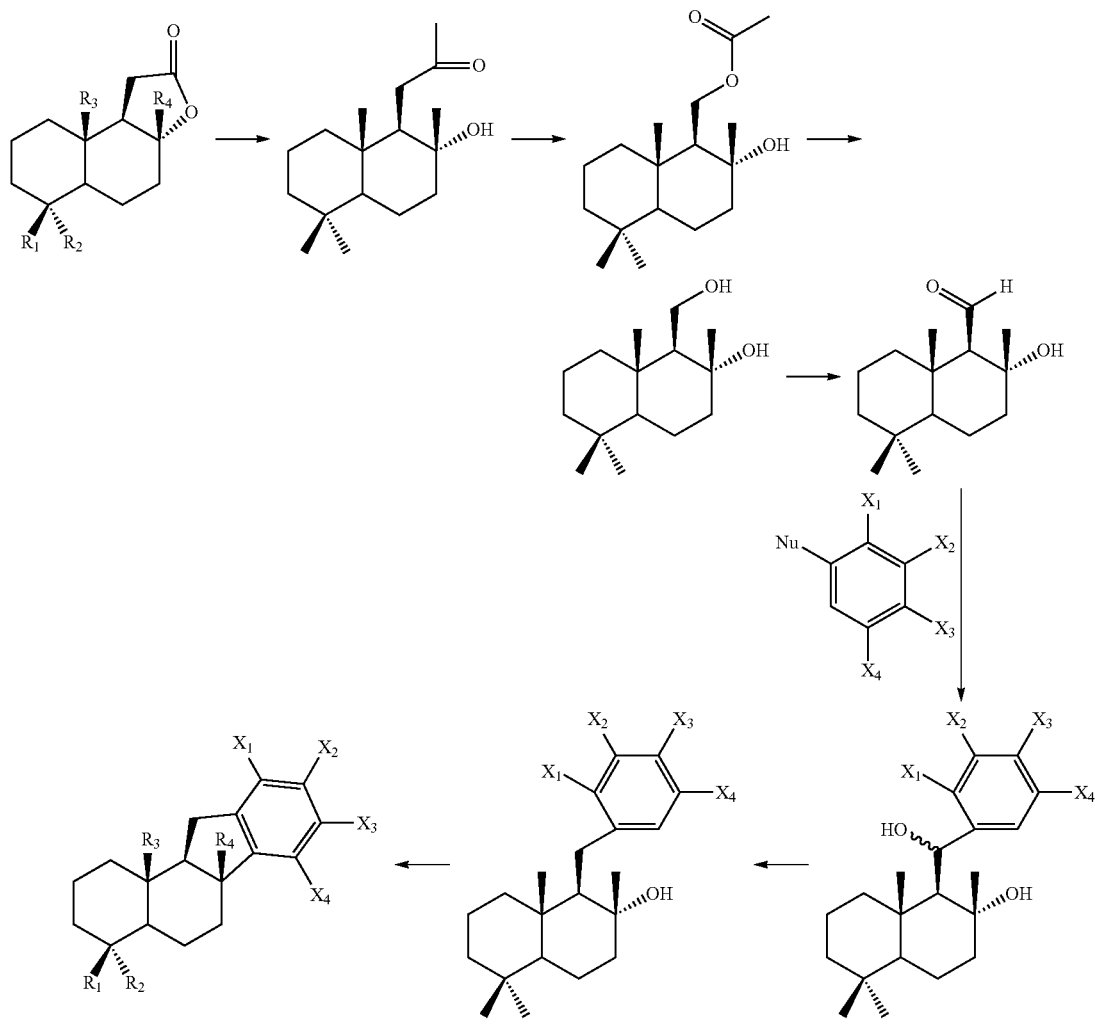
TABLE 2
Synthesis of Homopelorol and Homopelorol Analogs
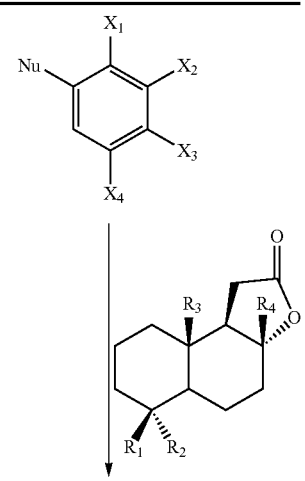

TABLE 2-continued

Synthesis of Homopelorol and Homopelorol Analogs

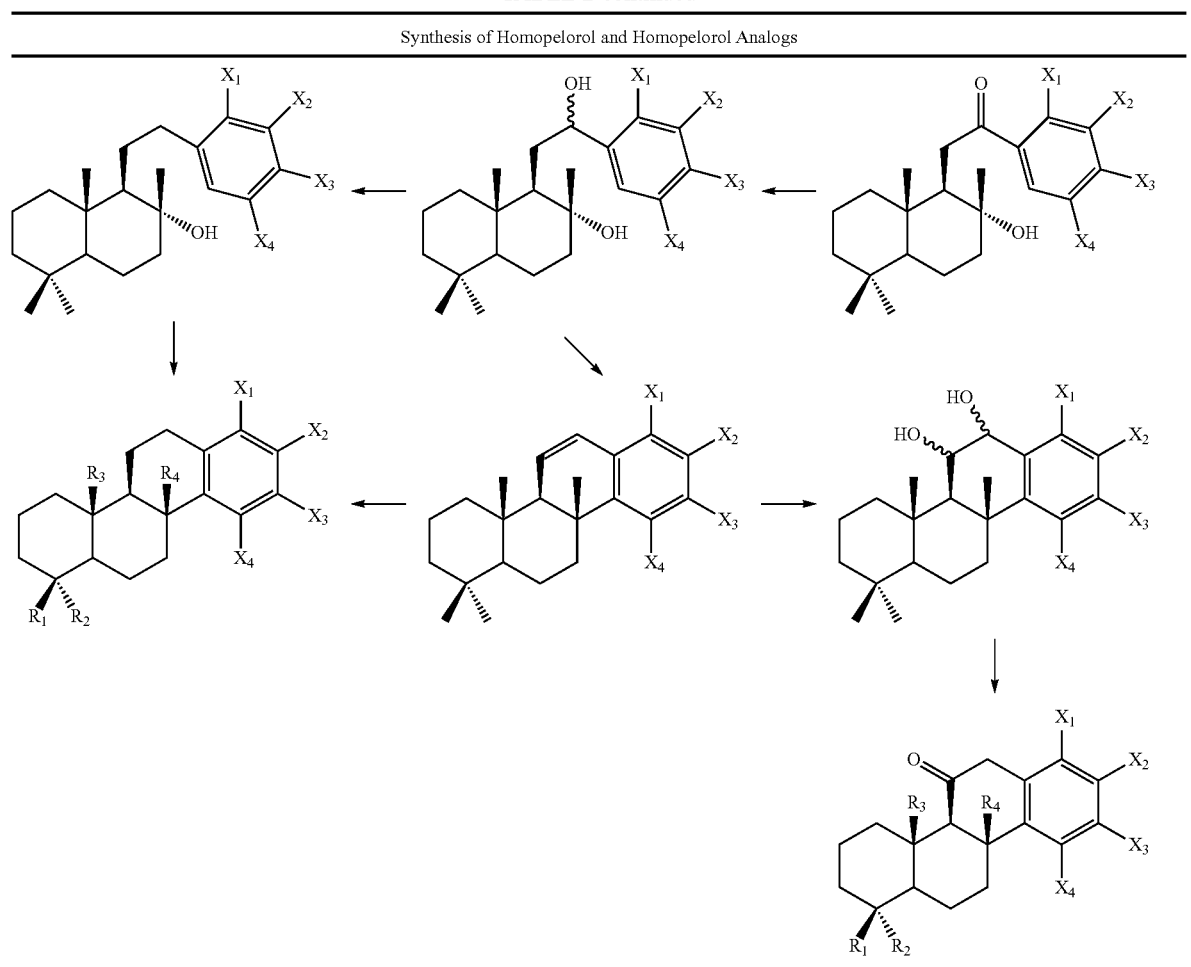

Pharmaceutical Compositions, Dosages, Administration and Indications

Compounds for use in this invention may be formulated into pharmaceutical compositions in any number of ways, which would be known to a person of skill in the art, all of which are within the scope of the invention. The person of skill in the art may be expected to select appropriate pharmaceutically acceptable salts as well as appropriate pharmaceutically acceptable excipients, diluents, and carriers.

Compounds according to the invention can be provided alone or in combination with other agents (for example, small molecules, peptides, or peptide analogues) in therapeutically- or prophylactically-acceptable amounts, in any pharmaceutically acceptable carrier. Methods well known in the art for making such pharmaceutical formulations are found in, for example, "Remington's Pharmaceutical Sciences" (19$^{th}$ edition), ed. A. Gennaro, 1995, Mack Publishing Company, Easton, Pa., incorporated by reference herein. Pharmaceutical formulations according to the present invention may, for example, contain excipients, sterile water, or saline, ethanol, methanol, dimethyl sulfoxide, polyalkylene glycols such as polyethylene glycol, propylene glycol, or other synthetic solvents, oils of vegetable origin, or hydrogenated napthalenes.

Compounds according to the invention may include hydrophobic compounds, for example, compounds that are substantially insoluble in water, but are freely soluble in solvents such as, for example, ethanol, methanol, dimethyl sulfoxide, or chloroform, or combinations thereof. Formulations containing such hydrophobic compounds may be provided using, for example, micelles, which are formed by amphiphilic compounds under certain conditions. In aqueous solutions, micelles are capable of incorporating hydrophobic compounds in their hydrocarbon cores, or within the micelle walls. Hydrophobic compounds may also be provided by solubilization in triglycerides (oils), for example, a digestible vegetable oil. The solubilized hydrophobic compound in the oil phase may be dispersed in an aqueous solution and stabilized using emulsifying agents, if desired. Alternatively, the hydrophobic compound may be provided in oil and delivered, for example, to the gastrointestinal system where bile salts may function as in vivo emulsifiers. Hydrophobic compounds may also be provided as microemulsions which, like emulsions, are liquid dispersions of oil and water, but have smaller particles with an oil phase in a micelle-like "core." Hydrophobic compounds according to the invention may also be provided together with a polymeric carrier, for example, a carbohydrate such as starch, cellulose, dextran, cyclodextrin, methylcellulose, or hyaluronic acid, or a polypeptide, such as albumin, collagen, or gelatin. Other modes of formulation of hydrophobic compounds may include liposomes, natural and synthetic phospholipids, or solvents, for example, dimethyl sulfoxide or alcohols.

The pharmaceutical compositions of the invention may be formulated so as to provide controlled release of the active compound(s) over a period of time. Thus, the formulations could contain, for example, an amount of the compound that would be toxic if administered as a single dose, but whose controlled release does not exceed toxic levels. Biocompatible, biodegradable lactide polymer, lactide/glycolide copolymer, or polyoxyethylene-polyoxypropylene copolymers, for example, may be used to control the release of the compounds. Other potentially useful delivery systems for modulatory compounds according to the present invention include ethylene-vinyl acetate copolymer particles, osmotic pumps, implantable infusion systems, and liposomes.

A "therapeutically effective amount" of a compound is an amount effective, at dosages and for periods of time necessary, to achieve the desired therapeutic result using a compound according to the invention. A therapeutically effective amount is also one in which any toxic or detrimental effects of the compound are outweighed by the therapeutically beneficial effects. A "prophylactically effective amount" of a compound refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount. Amounts considered sufficient will vary according to the specific compound used, the mode of administration, the stage and severity of the disease, the age, sex, weight, and health of the individual being treated, and concurrent treatments.

A preferred range for therapeutically or prophylactically effective amounts of the compounds of the invention may be 0.1 nM-0.1M, 0.1 nM-0.05M, 0.05 nM-15 µM or 0.01 nM-10 µM. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. Dosage regimens may be adjusted to provide the optimum therapeutic response. For example, a single bolus may be administered, several divided doses may be administered over time or the dose may be proportionally reduced or increased as indicated by the exigencies of the therapeutic situation.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Conventional pharmaceutical practice may be employed to provide suitable formulations or compositions to administer the compounds to patients, depending on the therapeutic or prophylactic objectives. Any appropriate route of administration may be employed, for example, systemic, parenteral, intravenous, subcutaneous, transdermal, transmucosal, intramuscular, intracranial, intraorbital, ophthalmic, intraventricular, intracapsular, intraspinal, intracisternal, intraperitoneal, intranasal, aerosol, topical, surgical, or oral administration. The formulations used may vary according to the chosen route of administration. Thus, for oral administration, the formulations may be in the form of tablets or capsules; for inhalants, the formulations may be in the form of powders, nasal drops, or aerosols; for transmucosal administration, the formulations may be nasal sprays or suppositories; for transdermal administration, the formulations may be creams, ointments, salves, or gels; etc.

Therapeutically effective or prophylactically effective amounts of SHIP 1 modulators and pharmaceutical compositions of this invention may be administered to patients in need of treatment or prophylaxis for cancer (neoplastic diseases), other cell proliferative disorders, inflammatory diseases and immune diseases. Neoplastic diseases include but are not limited to: leukemias, carcinomas, sarcoma, melanomas, neuroblastoma, capillary leak syndrome and hematological malignancies. Diseases with an inflammatory component include, but are not limited to: rheumatoid arthritis, multiple sclerosis, Guillan-Barre syndrome, Crohn's disease, ulcerative colitis, inflammatory bowel syndrome, psoriasis, graft versus host disease, host versus graft, lupus erythematosis, Alzheimer's disease and insulin-dependent diabetes mellitus. Diseases related to inappropriate activation of macrophage-related cells of the reticuloendothelial lineage include osteoporosis.

Pelorol and other compounds having the structure of Formula I exhibit SHIP 1 agonist activity. By activating SHIP 1, such agonists are particularly useful in the treatment of inflammatory diseases such as sepsis/septic shock, colitis, inflammatory bowel syndrome, and those involving macrophage proliferation or activation; neoplastic diseases such as myeloid and lymphoid leukemias; as an immunosuppressive agent such as in transplant rejection; hematopoietic disorders; and for affecting mast cell degeneration such as in the treatment or prevention of allergies.

EXAMPLE 1

In a preliminary screen of 150 marine organism extracts, extracts which activated SHIP 1 in an enzyme assay were identified. Assay-guided fractionation of one of these extracts resulted in the identification of the active compound as being pelorol (FIG. 1). The origin and processing of the extracts which tested positive in the screen and the nature of the assay were as follows.

Specimens of the brownish sheet sponge *Dactylospongia elegans* (order Dictyoceratida, family Spongiidae) were collected by hand using SCUBA at a depth of 5-10 m from a protected overhang in Rasch Passage on the outer reef of Madang Lagoon, Papua New Guinea, in January 1995. Freshly collected sponge was frozen on sight and transported to Vancouver, Canada over dry ice. The sponge was identified and for verification, a voucher sample was placed in the Zoological Museum of Amsterdam (ZMA POR. 15986). The frozen sponge (120 g) was cut into small pieces, immersed in and subsequently extracted repeatedly with MeOH (3×250 mL). The combined methanolic extracts were concentrated in vacuo and then partitioned between EtOAc (4×100 mL) and $H_2O$ (300 mL). The combined EtOAc extract was evaporated to dryness in vacuo to yield 490 mg of a brownish purple oil, found to contain pelorol.

The assay was performed in 96-well microtitre plates. SHIP 1 enzyme was produced with a hemagglutinin and a hexahistidine tag, from a mammalian expression vector. The His tag was employed to enhance purification. SHIP 1 enzyme (10 ng) was incubated with extract or DMSO for 15 minutes at room temperature before addition of 200 M inositol-1,3,4,5-tetrakisphosphate. The reaction was allowed to proceed for 20 minutes at 37 degrees C. The amount of inorganic phosphate released was then assessed by the addition of malachite green reagent followed by an absorbance measurement at 650 nm.

EXAMPLE 2

Pelorol was prepared according to the following scheme, under the specific conditions described below.

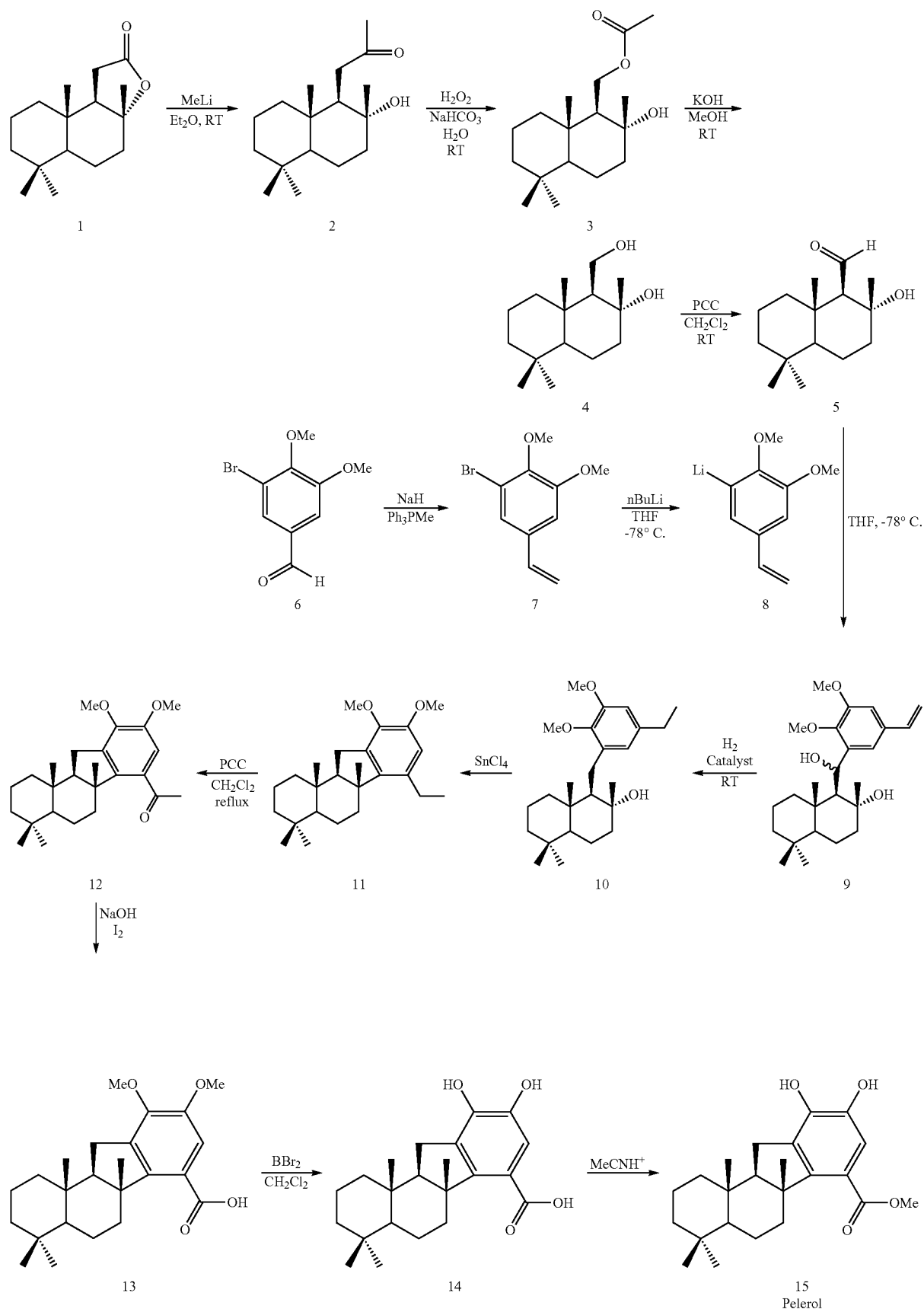

To a stirred solution of 1 (1.00 g, 3.99 mmol) in anhydrous Et$_2$O (30 mL) was added a freshly prepared 1.6M solution of MeLi in Et$_2$O (3 mL, 4.8 mmol) in portions for 10 min at r.t. and stirring was continued for another 5 min. The mixture was then treated with 10% HCl (2 mL), then transferred to a funnel and extracted with ethereal repeatedly. The combined extracts was washed with NaHCO$_3$ and H$_2$O, dried (MgSO$_4$), filtered and concentrated. The residue was column chromatographed with hexane/Et$_2$O (6:4) to give 0.74 g (70%) of 2.

To a stirred, cooled (ice bath) solution of (CF$_3$CO)$_2$O (9 mL, 63.85 mmol) in CH$_2$Cl$_2$ (40 mL) was added 50% aq H$_2$O$_2$ (1.8 mL, 31.66 mmol) and the mixture was allowed to stand in an ice bath for 10 min All subsequent operations were performed at r.t. The solution was treated with solid NaHCO$_3$ (5.40 g, 64.28 mmol) for 2 min and after stirring the mixture for 8 min, a solution of 2 (1.80 g, 6.76 mmol) in CH$_2$Cl$_2$ (54 mL) was added. The resulting mixture was stirred for 30 min and then, after addition of H$_2$O (10 mL), was treated with solid NaHCO$_3$ in portions for 45 min until the pH reached 7. Finally, the mixture was extracted with Et$_2$O. The combined extracts were washed with NaHCO$_3$, H$_2$O and dried (MgSO$_4$), filtered and concentrated to give pure 3.

Compound 3 (1 g, 3.6 mmol) was dissolved in 10% solution of KOH in MeOH (1 mL, 1.78 mmol) at 0° C. The resulting mixture was stirred for 10 min. After addition of H2O, the solution was extrated with Et2O. The extrated was washed with H$_2$O, dried (MgSO$_4$), filtered and concentrated to give 0.8 g of 4.

In an oven dried, N$_2$ flushed 100 mL round bottom flask equipped with a magnetic stirring bar was placed 3.24 g (15 mmol) of PCC, 30 mL of CH$_2$Cl$_2$ and 2.4 g (10 mmol) of 4. The mixture was well stirred at r.t. for 2 hrs and was quenched by adding 30 mL of Et$_2$O. The resulting solution was filtered through a thick pad of silica gel and concentrated to give a residue. The residue was column chromatographed with hexane/EA (8:2) to give 1.6 g (67%) of 5.

Sodium hydride (24.6 mg, 0.82 mmol, 80% oil dispersion) and dry THF (5 mL) were added to a dry flask equipped with a condenser and dry N$_2$ flow. To this suspension was added methyl triphenyl phosphonium bromide (0.146 g, 0.41 mmol) and the mixture was stirred for 10 min. Then 6 (100 mg, 0.41 mmol) in THF (2 mL) was added and the mixture was gently reflux for 2 h. The reaction was quenched by adding 2 mL of methanol and then extracted with Et$_2$O. After usual work up treatment. 94.3 mg of 7 was afforded.

A 1.6M solution of tBuLi in pentane (1.74 mL, 2.79 mmol) was added slowly to a stirred solution of 7 (612.6 mg, 2.52 mmol) in dry THF (20 mL) at −78° C. After stirring for 30 min, a solution of 5 (300 mg, 1.26 mmol) in dry THF (5 mL) was added. The mixture was further stirred at −78° C. for 2 hrs. Then H$_2$O (10 mL) was added and the mixture was extracted with Et$_2$O (120 mL twice). The combined Et$_2$O extracts were washed with sat.brine, dried (MgSO$_4$) and concentrated to give a residue, which was chromatographed on NP Sepak™ to give 280 mg (55%) of 9.

A solution of 9 (40 mg, 0.1 mmol) in EA (5 mL) was hydrogenated over 10% Pd/C (50 mg) under an atmosphere of hydrogen at r.t. over night. Filtration and concentration gave 37 mg (96%) of 10.

To a stirred solution of 10 (38.8 mg, 0.1 mmol) in CH$_2$Cl$_2$ (10 mL), SnCl$_4$ (0.1 mL) was added slowly at −20° C. under argon for 2 min. The resulting mixture was further stirred for 20 min and then diluted with CH$_2$Cl$_2$ (20 mL) and poured into ice. The aqueous phase was extracted with CH$_2$Cl$_2$ twice (20 mL) and combined the extracts, washed with saturated NaHCO3, saturated brine and dried over MgSO$_4$. Evaporation to afford 11 (28 mg, 76%).

PCC (41.6 mg, 0.192 mmol) was added to 11 (7.4 mg, 0.02 mmol) dissolved in 2 mL of CH$_2$Cl$_2$. The mixture was stirred at gentle reflux for 24 hrs under Argon. The reaction was diluted with Et$_2$O (20 mL) and the resulting dark solution was filter through a NP Sepak™. Concentration of the filtrates and further purification afford 1.5 mg (20%) of 12.

1.5 mg of 12 was dissolved and stirred in 2 mL of NaOH (10%) solution (containing 0.5 mL THF). 5 mg Iodine is added subsequently and the mixture was further stirred for 20 min and acidified by adding 3 mL of 10% H$_2$SO$_4$. The solution was extracted with 50 mL of Et$_2$O, washed with saturated brine and concentrated to afford a residue 13.

38.6 mg (0.1 mmol) of 13 was stirred in CH$_2$Cl$_2$ (1 mL) under Argon. BBr$_3$ in CH$_2$Cl$_2$ (2.0 mL 1M) was added, and stirring was continued for 1.5 h. The mixture was then poured into H$_2$O and extracted with CH$_2$Cl$_2$ (50 mL). The combined extracts were then dried over MgSO$_4$, filtered and concentrated. The residue was purified by NP Sepak™ (hexane:EA=7:3) to afford 14 (25 mg, 70%).

35.8 mg (0.1 mmol) of 14 was dissolved in MeOH (2 mL) containing 5% H$_2$SO$_4$. Stirring was continued for 2 hr and the mixture was extracted with Et$_2$O, dried over MgSO$_4$ and concentrated to afford 15.

EXAMPLE 3

The pelorol analog PNSR-15A was synthesized following the methodologies described in Example 3 using the following scheme.

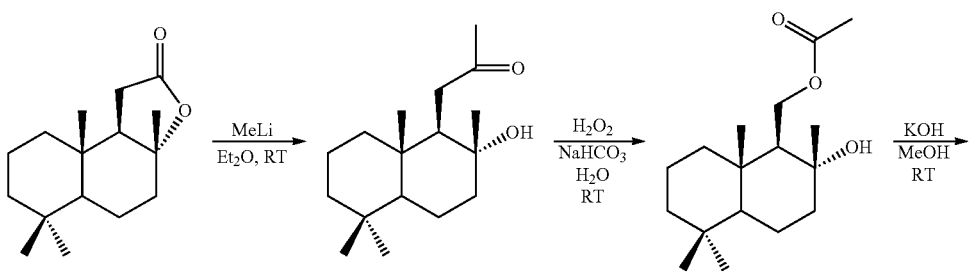

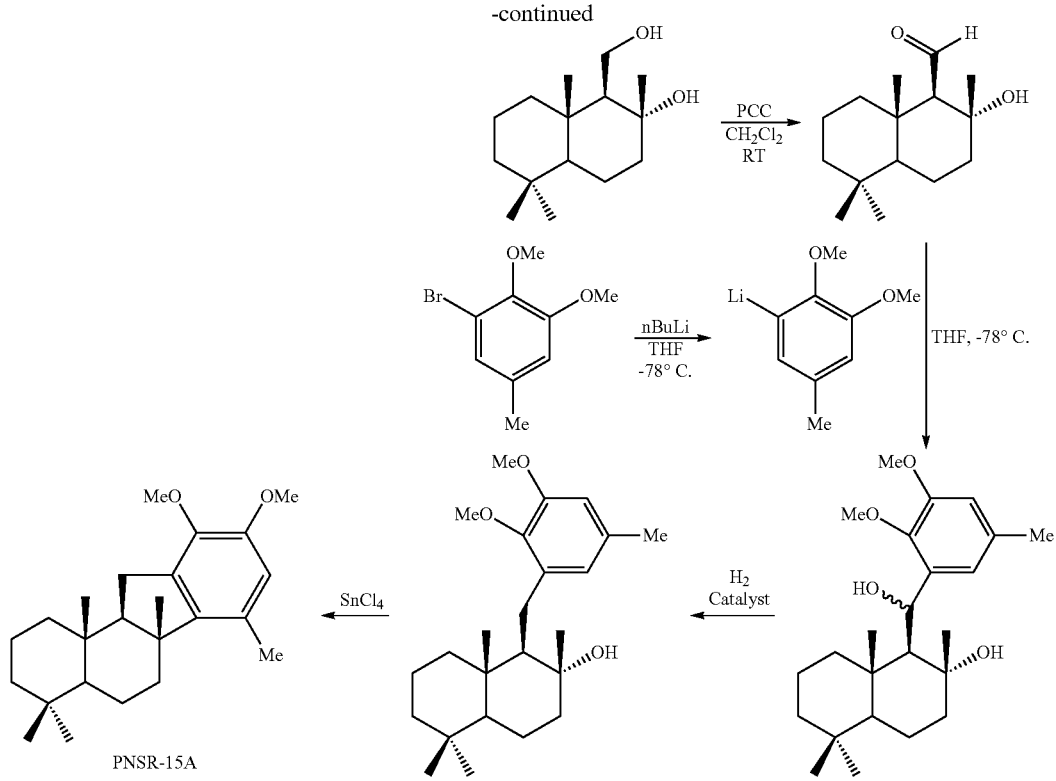
EXAMPLE 4
The homopelorol analog PNSR-4A was synthesized by the methodologies described above and according to the following scheme.
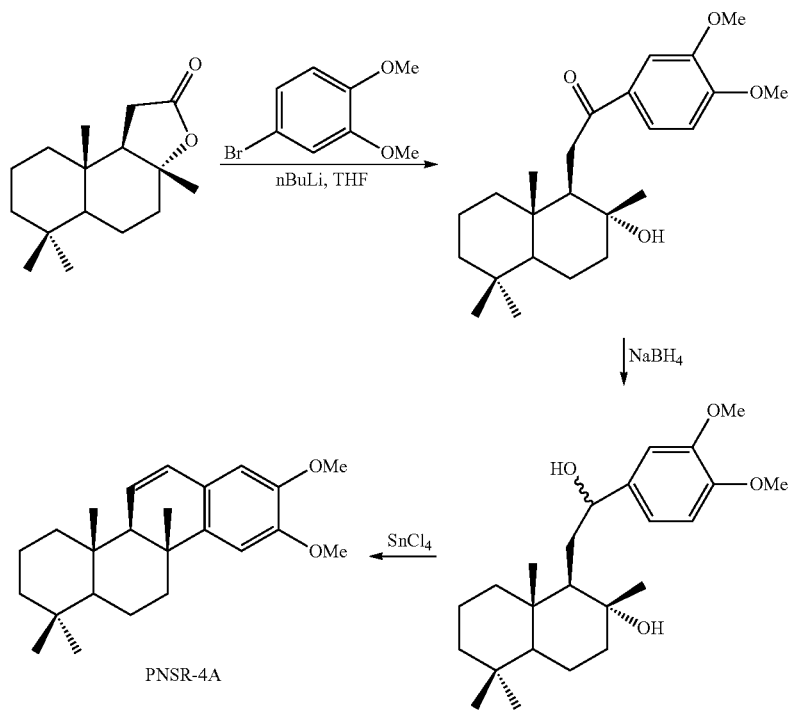

EXAMPLE 5
The homopelorol analog PNSR-14A was synthesized by the methodologies described above and according to the following scheme.
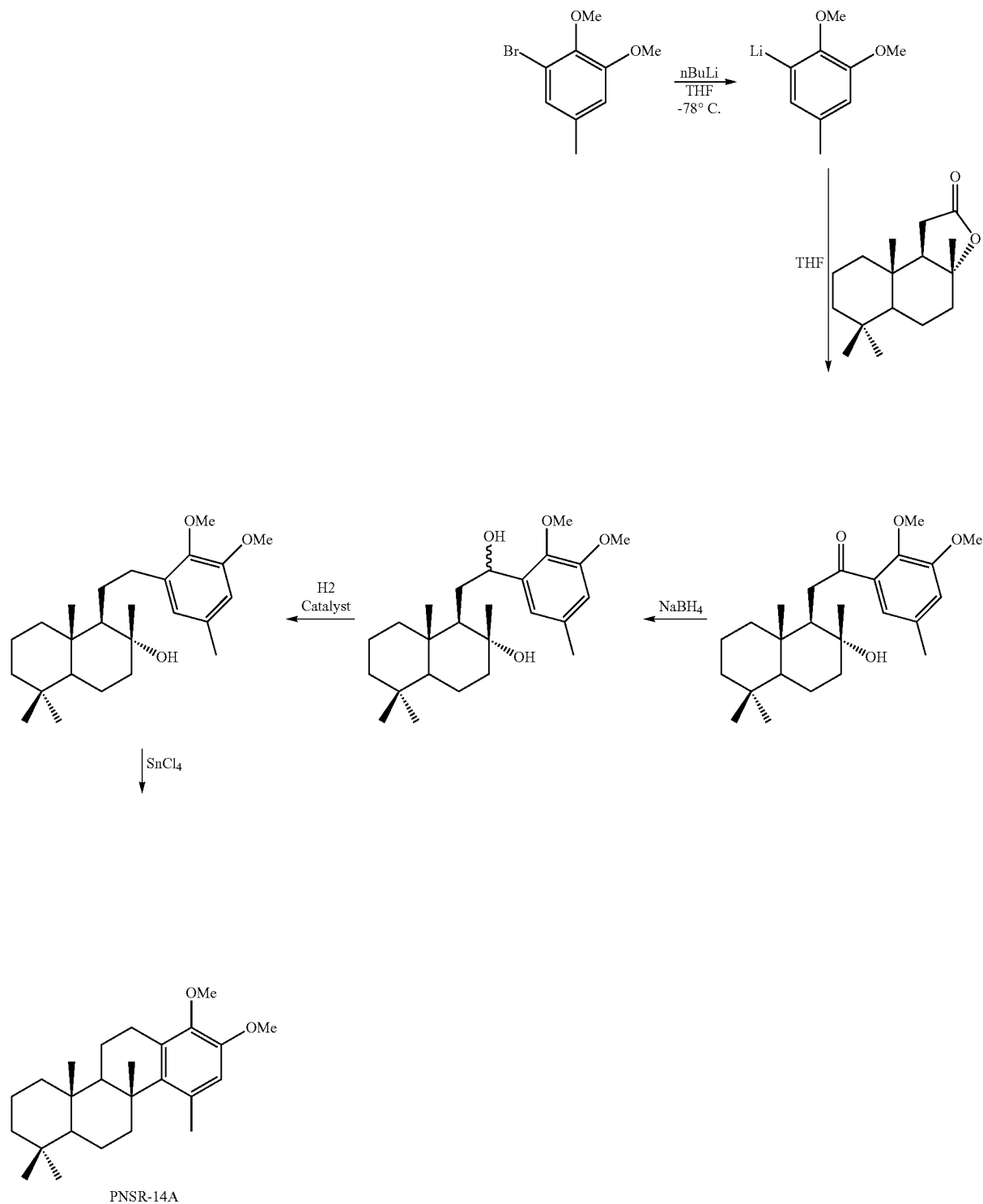

EXAMPLE 6
Homopelorol may be synthesized according to the following scheme based on the preceding examples and following the methodologies described above.
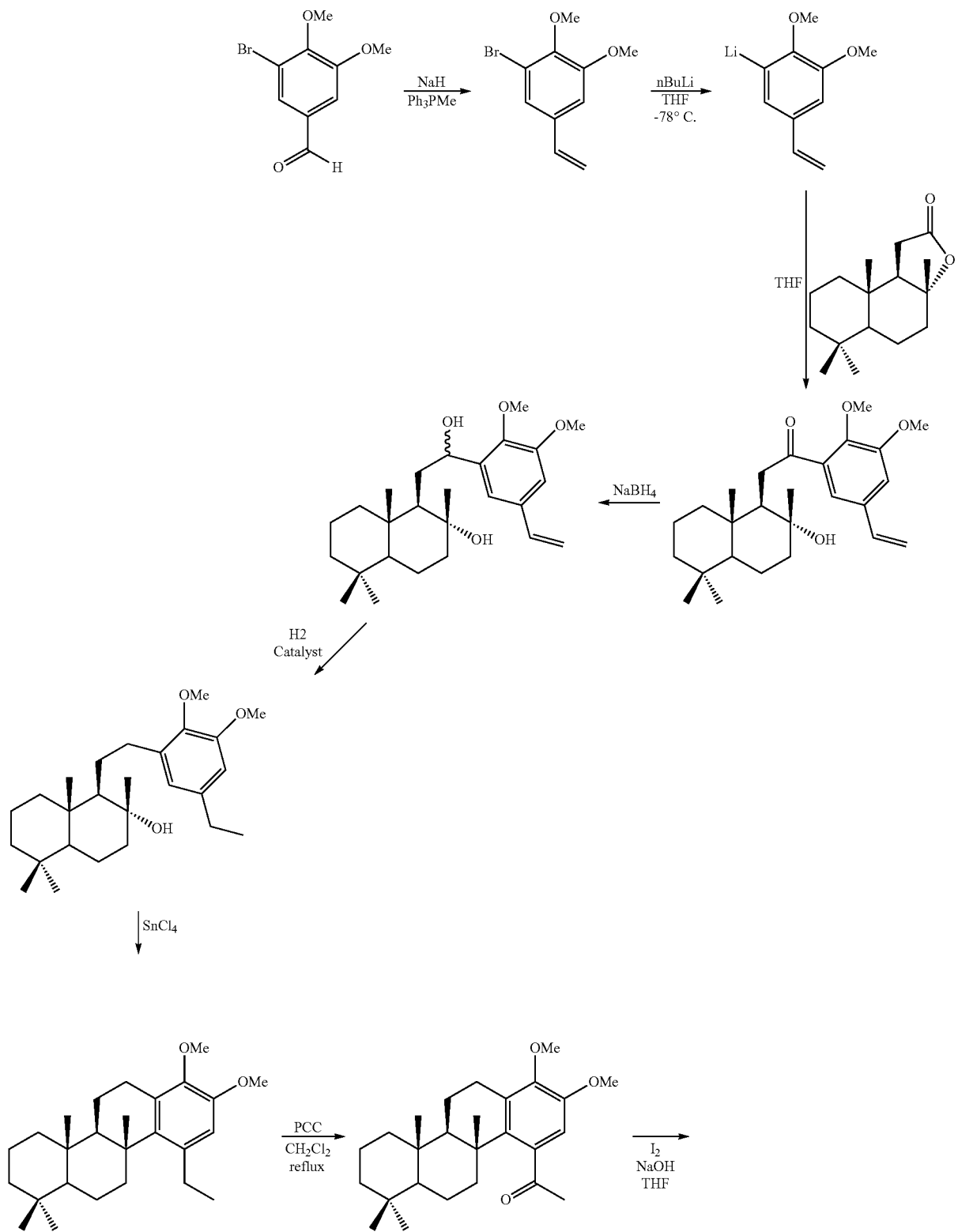

-continued

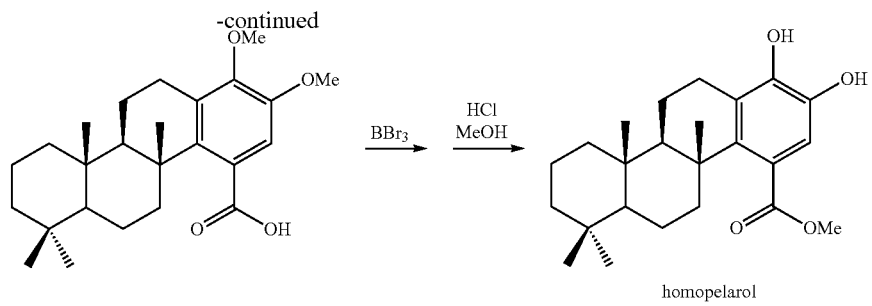

homopelarol

EXAMPLE 7

Figure 2:
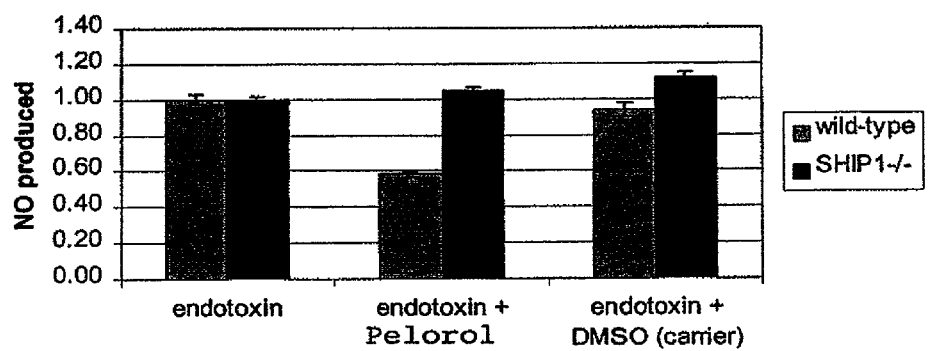
FIG. 2 is a graph depicting the effect of pelorol on macrophage nitric oxide (NO) production.
Figure 3:
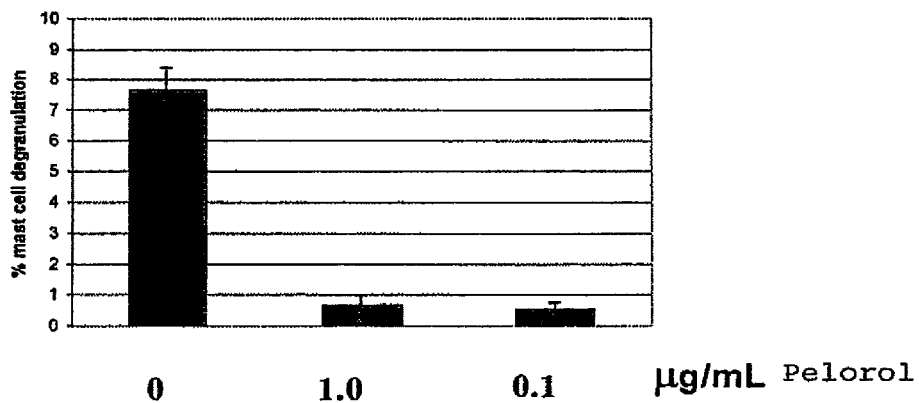
FIG. 3 is a graph depicting the effect of pelorol on IgE mediated mast cell activation.

In addition to causing an increase in activity in the SHIP 1 enzyme assay described for FIG. 1, agonist compounds of Formula I exhibit anti-inflammatory actions on macrophages and mast cells in intact cell-based assays, inhibit nitric oxide production from endotoxin activated wild-type macrophages and exhibit anti-inflammatory actions on live subjects. Results obtained for pelorol in NO release and mast cell activation assays are shown in FIGS. 2 and 3, respectively Inhibition of NO release was not observed in SHIP 1−/− macrophages. Pelorol significantly reduced IgE induced mast cell degranulation.

Procedures used in the cell and animal based assays are described below. Results for pelorol and various analogs within Formula I are shown in Table 3, including results using the enzyme assay described in Example 1.

For the NO release assay, wild-type or SHIP 1−/− macrophage cells were aliquoted into microtitre plates ($5 \times 10^4$/well) and activated with 1 g/mL endotoxin (LPS) in the presence or absence of test compound or DMSO carrier. The cells were incubated at 37° C., 5% $CO_2$ for 24 hours and the culture supernatant was removed for NO determination using the Griess reagent. Alternatively, J774.1a macrophage cells were treated with 10 ng/ml of test compound dissolved in DMSO for 40 minutes prior to the addition of LPS. Culture supernatants were collected after 24 hr. for determination of NO concentration using the Griess reagent.

For the mast cell activation assay, bone marrow derived mast cells were incubated at 4° C. with anti-DNP IgE for 1 hr. They were then washed twice with 23° C. Tyrode's buffer, and incubated in the presence of test compound or vehicle control for 30 minutes before a 15 minute treatment with DNP-human serum albumin. The degree of degranulation was determined by measuring the release of β-hexosaminidase.

For the macrophage TNF-α production assay, J774.1a macrophage cells were treated with 10 ng/mL of test compound dissolved in cyclodextrin for 40 minutes prior to the addition of 100 ng/mL LPS. Culture supernatants were collected after 2 hr and 5 hr for TNF-α determination by ELISA.

The mouse ear edema (Evans Blue) assay is a standard model for allergic inflammation. Mice were passively sensitized by intravenous injection of monoclonal anti-DNP IgE antibody. 24 hours later, 10 ng test compound (right ears) in 20 µl DMSO:Methanol (1:3) or vehicle alone (left ears) were applied 20 minutes followed by application of the inducing agent [20 µl of 0.15% DNFB in acetone:olive oil (4:1)]. Mice were then injected intravenously with 300 µl 1% Evans Blue. Vascular permeability was measured at 1 hr after application of the inducing agent by visual inspection and quantification of Evans Blue extravasation in the ear. To quantify the Evans Blue content, ears were harvested at 1 hr post DNFB treatment and Evans Blue was extracted by incubation in formamide at 37° C. for 24 hr and quantified by spectophotometry at 620 nm. Ears pretreated with carrier alone mounted a prompt anaphylactic reaction in response to DNFB challenge. In contrast, SHIP 1 agonists showed a clear inhibition of vascular permeabilization as shown by decreased Evans Blue extravasation.

The mouse ear edema (lymphocyte infiltration assay) is a contact hypersensitivity or ear inflammation model and is a standard in vivo model for human allergy. Contact hypersensitivity consists of an initial sensitizing phase and an elicitation phase. The latter phase occurs when the epidermal cells encounter a particular antigen to which they have previously been exposed and is characterized by localized immune cell infiltration, inflammation, and edema. In this assay, female 4 week old (20 g) Balb/c mice were sensitized to the haptenizing agent, 2,4-dinitrofluorobenzene (DNFB) by shaving their abdominal region with an electric razor before applying 25 µl of 0.5% DNFB in acetone:olive oil (4:1, v/v) to the abdominal wall for two consecutive days. Four days after the second application, mice were lightly anesthesized with halothane before being challenged (treated) epicutaneously on each side of the right and left ear with 10 µl of 0.2% DNFB. All mice received a 500 µl intraperitoneal (i.p.) injection of [$^3$H]-methyl thymidine in sterile saline (1 µCi/g body weight) 24 hours before epicutaneous challenge with DNFB. Thirty minutes prior to DNFB challenge, the right and left ears were pretreated with test compound in DMSO:methanol (1:3, v/v) or vehicle alone, respectively. Twelve hours following DNFB challenge, mice were sacrificed by $CO_2$ asphyxiation and 8 mm diameter plugs were taken from each ear and digested in 500 µl Solvable™ at 60° C. for 10-12 hours. Samples were decolourized by the addition of $H_2O_2$ and analyzed for radio-labelled leukocyte infiltrates by standard liquid scintillation counting.

The colitis assay is based on determining whether a test compound protects mice from TNBS (trinitrobenzene sulfonic acid) induced inflammation. Test compound (10 mg/kg) or vehicle control was injected intraperitoneally into mice just prior to a TNBS enema administration. After 2 days, the colons of the vehicle treated mouse were severely inflamed while the SHIP 1 agonist treated mouse had no signs of inflammation.

TABLE 3

| | SHIP enzyme assay | Macrophage NO production | Macrophage TNFα production | Mast cell activation | Mouse ear edema (evans blue assay) | Mouse ear edema (leukocyte infiltration assay) | colitis |
|---|---|---|---|---|---|---|---|
| Pelorol | +++ | +++ | +++ | +++ | +++ | ND | +++ |
| Dimethoxypelorol | + | +++ | ND | ND | ND | ND | ND |
| PNSR-4A | insol | ND | ND | ND | +++ | ND | ND |
| PNSR-15A | ND | ND | ND | ND | ND | ++ | ND |
| PNSR-16A | ND | ND | +++ | ND | ND | ++ | ND |
| PNSR-17A | ND | ND | ++ | ND | ND | ND | ND |
| PNSR-18A | ND | ND | +++ | ND | ND | ND | ND |

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

REFERENCES

1. Huber, M. et al. (1999) *Prog Biophys Mol Biol* 71:423.
2. Sattler, M. et al. (1999) *Mol Cell Biol* 19:7473.
3. Lui, Ling et al. (2001) *Blood* 98:1225 (Abstract No. 1225).
4. Kwak, J. H. et al. (2000) *J. Nat. Prod.* 63:1153-56.
5. Goclik, E. et al. (2000) *J. Nat. Prod.* 63:1150-52.
6. Ishihara, Kazuaki et al. (2001) *J. of the American Chem. Soc.* 123:1505-1506.
7. Ishihara, Kazuaki et al. (2002) *J. of the American Chem. Soc.* 124:3647-3655.
8. Rosales, Viale et al. (2002) *J. of Organic Chem.* 67:1167-1170.
9. Corey, Elias J. et al. (1998) *Angewante Chemie*, Intl. Ed. 37:1126-1128.
10. Boreham, Christopher J. et al. (1995) *Organic Geochemistry* 23:461-6.
11. Freeman, Katherine H. et al. (1994) *Organic Geochemistry* 21:1037-1049.
12. Schaeffer, Phillipe et al. (1994) *Angewante Chemie* 106:1235-8.
13. Harrington, Scott R. et al. (1994) *Tetrahedron* 50:9229-54.
14. Registry Number 112299-69-1
15. Helgason, C. D. et al. (1998) *Genes Dev.* 12:1610.
16. Helgason, C. D. et al. (2000) *J. Exp. Med.* 191:781.
17. O'Farrell, A. M. et al. (2000) *J. Immunol.* 164:4607.
18. Damen, J. E. et al. (1998) *Blood* 92:1199.

We claim:

1. A compound of Formula I or a salt thereof,

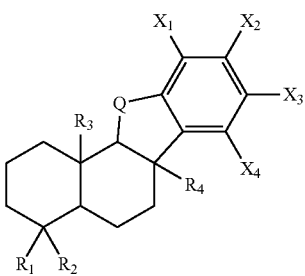

I wherein;
$R_1$ and $R_2$ are independently selected from the group consisting of: —$CH_3$, —$CH_2CH_3$, —$CH_2OH$, —$CH_2OR'$, —CHO, —$CO_2H$, and —$CO_2R'$;
$R_3$ and $R_4$ are independently selected from the group consisting of: H, —$CH_3$, —$CH_2CH_3$, —$CH_2OH$, —$CH_2OR'$, —CHO, —$CO_2H$, and —$CO_2R'$;
Q is —$CH_2$—;
$X_1$, $X_2$, $X_3$, and $X_4$ are independently selected from the group consisting of: H, R, OH, —OR, —$CO_2H$, —$CO_2R'$, F, Br, Cl, I, —CN, —$SO_3H$, —$OSO_3H$, $NO_2$, $NH_2$, —NHR, and —$NR_2$;
where R is a linear, branched, or cyclic, saturated or unsaturated one to ten carbon alkyl group that is unsubstituted or is substituted with one or more of: OH, =O, SH, F, Br, Cl, I, $NH_2$, —NHR', —$NR'_2$, $NO_2$, —$CO_2H$, —$CO_2R'$, and epoxide;
and R' is a linear, branched, or cyclic, saturated or unsaturated one to ten carbon alkyl group that is unsubstituted or substituted with one or more of: OH, =O, SH, F, Br, Cl, I, $NH_2$, —NHR", —$NR"_2$, $NO_2$ and —$CO_2H$ where R" is a linear, branched, or cyclic, saturated or unsaturated one to ten carbon alkyl group;
providing that the compound does not have the following precise structure of pelorol:

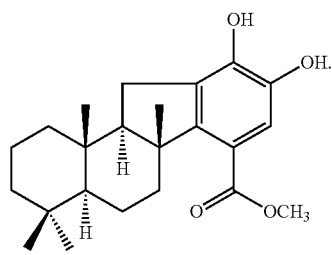

2. The compound of claim 1, wherein $R_1$ is methyl, ethyl, —$CH_2OH$, or —$CH_2OR'$.
3. The compound of claim 1, wherein $R_2$ is methyl, ethyl, —$CH_2OH$, or —$CH_2OR'$.
4. The compound of claim 1, wherein R' in $R_1$ is limited to methyl, ethyl, propyl or butyl.
5. The compound of claim 1, wherein R' in $R_2$ is limited to methyl, ethyl, propyl or butyl.
6. The compound of claim 1, wherein $R_1$, $R_2$, $R_3$ and $R_4$ are methyl.
7. The compound of claim 1, wherein $X_1$ is H, OH, R, OR, —$CONH_2$, —CONHR', or —COR'.
8. The compound of claim 1, wherein $X_2$ is H, OH, R, OR, —$CONH_2$, —CONHR', or —COR'.

9. The compound of claim 1, wherein $X_3$ is H, OH, R, OR, —$CONH_2$, —CONHR', or —COR'.

10. The compound of claim 1, wherein R and R' in one or more of $X_1$, $X_2$, and $X_3$ are limited to methyl, ethyl, propyl and butyl.

11. The compound of claim 1, wherein $X_1$ is H, OH, or —$OCH_3$.

12. The compound of claim 11, wherein $X_2$ is H, OH, or $OCH_3$.

13. The compound of claim 6, wherein $X_1$ and $X_2$ are independently selected from H and OH.

14. The compound of claim 1, wherein $X_3$ is H, OH, or $OCH_3$.

15. The compound of claim 1, wherein $X_4$ is H, R, OH, OR, $CO_2H$ or $CO_2R'$.

16. compound of claim 13, wherein $X_3$ and $X_4$ are independently selected from H, methyl, ethyl, propyl and butyl.

17. The compound of claim 13, wherein $X_3$ is H and $X_4$ is methyl.

18. The compound of claim 1, selected from: PNSR-16A and PNSR-18A.

19. The compound of claim 1, having the configuration S, R, R, S at C-5, C-8, C-9 and C-10 respectively.

20. The compound of claim 1, having the configuration R, S, S, R at C-5, C-8, C-9 and C-10 respectively.

21. A pharmaceutical composition comprising a pharmaceutically acceptable carrier and one or more compounds of Formula I or pharmaceutically acceptable salts thereof,

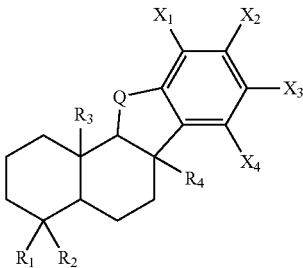

I wherein;

$R_1$ and $R_2$ are independently selected from the group consisting of: —$CH_3$, —$CH_2CH_3$, —$CH_2OH$, —$CH_2OR'$, —CHO, —$CO_2H$, and —$CO_2R'$;

$R_3$ and $R_4$ are independently selected from the group consisting of: H, —$CH_3$, —$CH_2CH_3$, —$CH_2OH$, —$CH_2OR'$, —CHO, —$CO_2H$, and —$CO_2R'$;

Q is —$CH_2$—;

$X_1$, $X_2$, $X_3$, and $X_4$ are independently selected from the group consisting of: H, R, OH, —OR, —$CO_2H$, —$CO_2R'$, F, Br, Cl, I, —CN, —$SO_3H$, —$OSO_3H$, $NO_2$, $NH_2$, —NHR, and —$NR_2$;

where R is a linear, branched, or cyclic, saturated or unsaturated one to ten carbon alkyl group that is unsubstituted or is substituted with one or more of: OH, =O, SH, F, Br, Cl, I, $NH_2$, —NHR', —$NR'_2$, $NO_2$, —$CO_2H$, —$CO_2R'$, and epoxide;

and R' is a linear, branched, or cyclic, saturated or unsaturated one to ten carbon alkyl group that is unsubstituted or substituted with one or more of: OH, =O, SH, F, Br, Cl, I, $NH_2$, —NHR", —$NR"_2$, $NO_2$ and —$CO_2H$ where R" is a linear, branched, or cyclic, saturated or unsaturated one to ten carbon alkyl group.

22. The pharmaceutical composition of claim 21, wherein $R_1$, $R_2$, $R_3$ and $R_4$ are methyl.

23. The pharmaceutical composition of claim 22, wherein $X_1$ and $X_2$ are independently selected from H and OR.

24. The pharmaceutical composition of claim 23, wherein $X_3$ is hydrogen and $X_4$ is methyl.

* * * * *